US011376295B2

(12) United States Patent
Park et al.

(10) Patent No.: US 11,376,295 B2
(45) Date of Patent: Jul. 5, 2022

(54) **METHOD FOR PREPARING *RHUS VERNICIFLUA* STOKES EXTRACT CONTAINING INCREASED FISETIN CONTENT, AND METASTASIS-INHIBITING ANTICANCER AGENT COMPOSITION CONTAINING SAME**

(71) Applicant: MEDIENCE CO.,LTD, Chuncheon-si (KR)

(72) Inventors: Sang Jae Park, Yongin-si (KR); Kyoung Hee Kim, Chuncheon-si (KR)

(73) Assignee: Medience Co., Ltd, Chuncheon-si (KR)

( * ) Notice: Subject to any disclaimer, the term of this patent is extended or adjusted under 35 U.S.C. 154(b) by 76 days.

(21) Appl. No.: 16/975,981

(22) PCT Filed: Oct. 12, 2018

(86) PCT No.: PCT/KR2018/012007
§ 371 (c)(1),
(2) Date: Aug. 26, 2020

(87) PCT Pub. No.: WO2020/075887
PCT Pub. Date: Apr. 16, 2020

(65) Prior Publication Data
US 2021/0038667 A1 Feb. 11, 2021

(30) Foreign Application Priority Data
Oct. 10, 2018 (KR) .......................... 10-2018-0120176

(51) Int. Cl.
*A61K 36/22* (2006.01)
*A23L 33/115* (2016.01)
*A61P 35/04* (2006.01)
*A61K 31/353* (2006.01)

(52) U.S. Cl.
CPC ............ *A61K 36/22* (2013.01); *A23L 33/115* (2016.08); *A61K 31/353* (2013.01); *A61P 35/04* (2018.01); *A61K 2236/33* (2013.01); *A61K 2236/35* (2013.01)

(58) Field of Classification Search
None
See application file for complete search history.

(56) References Cited

U.S. PATENT DOCUMENTS

| 6,099,845 | A  | * | 8/2000  | Na .......................... A61K 36/22 424/779 |
| 7,629,006 | B2 | * | 12/2009 | Choi ....................... A61P 25/28 424/725 |
| 8,551,537 | B2 | * | 10/2013 | Park ....................... A61K 31/352 424/725 |
| 8,859,014 | B2 | * | 10/2014 | Park ....................... A61K 31/353 424/725 |

FOREIGN PATENT DOCUMENTS

| CN | 1207309 A       | 2/1999  |
| CN | 103702675 A     | 4/2014  |
| JP | 11-49693 A      | 2/1999  |
| JP | 2013-535500 A   | 9/2013  |
| KR | 10-1999-014987 A| 3/1999  |
| KR | 10-2005-0107352 A| 11/2005 |
| KR | 10-1103040 B1   | 1/2012  |
| KR | 10-2012-0022678 A| 3/2012  |
| KR | 10-1314302 B1   | 10/2013 |
| KR | 1314302       * | 10/2013 |
| KR | 10-2017-0082249 A| 7/2017  |

OTHER PUBLICATIONS

Lee, S. et al. Comparison of the Main Components and Bioactivity of Rhus verniciflua Stokes Extracts . . . BMC Complementary and Alternative Medicine 18:242, 2018. (Year: 2018).*
Ramona Turcas, et al., "Catalytic and stoichiometric flavanone oxidation mediated by nonheme oxoiron(IV) complexes as flavone synthase mimics: kinetic, mechanistic and computational studies", Dalton Transactions, The Royal Society of Chemistry, Sep. 13, 2018, pp. 14416-14420, vol. 47.
International Search Report for PCT/KR2018/012007 dated Jul. 9, 2019 (PCT/ISA/210).
"Chemical Technology", Yinxian Peng Harbin Engineering University Press, 2018, Abstract Only (1 page total).
Youngtaek Moon, "Palladium-Catalyzed Dehydrogenation/Oxidative Cross-Coupling Sequence of b-Heteroatom-Substitute d Ketones", Angewandte Chemie Intl Edit, 2012, Abstract Only (1 page total).
Chen Hongxia et al., "Research and Development of Natural Products", Research on sumac flavonoids, 2013, Issue 12, Abstract Only (1 page total).
Im, Won Kyun et al., "Fisetin-Rich Extracts of Rhus verniciflua Stokes Improve Blood Flow Rates in Mice Fed Both Normal and High-Fat Diets", Journal of medicinal food, vol. 19, No. 2, 2016, pp. 120-122 (4 page total).
Communication dated Apr. 19, 2022 which is issued by the Japanese Patent Office with regard to the counterpart Japanese Patent Application No. 2021-518886.

* cited by examiner

Primary Examiner — Ralph J Gitomer
(74) Attorney, Agent, or Firm — Sughrue Mion, PLLC

(57) ABSTRACT

A method for preparing a *Rhus verniciflua* Stokes extract with an increased content of fisetin, the method including adding reacting at least one catalyst selected from the group consisting of platinum, chromium, nickel, silicon, copper, and oxides of these metals, to a *Rhus verniciflua* Stokes extract or a concentrated *Rhus verniciflua* Stokes extract and conducting reaction to convert fustin contained in the *Rhus verniciflua* Stokes into fisetin, and a functional health food composition for preventing or ameliorating cancer, or an anticancer pharmaceutical composition for inhibiting metastasis of cancer, as a main component, containing the *Rhus verniciflua* Stokes extract with an increased content of fisetin, prepared by the method which provides a very safe and efficient method that is capable of preparing an extract that exhibits improved antioxidant activity and anticancer activity by increasing the content of the main functional ingredients of natural extracts, and an anticancer agent composition.

9 Claims, 2 Drawing Sheets

METHOD FOR PREPARING RHUS VERNICIFLUA STOKES EXTRACT CONTAINING INCREASED FISETIN CONTENT, AND METASTASIS-INHIBITING ANTICANCER AGENT COMPOSITION CONTAINING SAME

CROSS REFERENCE TO RELATED APPLICATIONS

This application is a National Stage of International Application No. PCT/KR2018/012007 filed Oct. 12, 2018, claiming priority based on Korean Patent Application No. 10-2018-0120176 filed Oct. 10, 2018, the entire disclosures of which are incorporated herein by reference.

TECHNICAL FIELD

The present invention relates to the preparation of a *Rhus verniciflua* Stokes extract, and more particularly to a method of preparing a *Rhus verniciflua* Stokes extract by converting fustin, which is one of the main components of *Rhus verniciflua* Stokes, into fisetin to obtain a *Rhus verniciflua* Stokes extract having more potent anticancer activity of fisetin, and an anticancer composition for inhibiting cancer metastasis containing the same.

BACKGROUND ART

The lacquer tree is a plant belonging to the lacquer family, and is classified as *Rhus verniciflua* Stokes and *R. trichocarpa* Miguel, and oriental lacquer refers to the sap exuded from wounds of these trees. The lacquer contains ingredients such as urushiol and flavonoids, and thus has anti-cancer, anti-aging, toxin removal, and liver detoxification effects owing to excellent anti-oxidation activity thereof, circulates blood throughout the body, warms the body, and is effective in treating chronic gastrointestinal disease through improvement in digestive function. In particular, *Rhus verniciflua* Stokes is known to have superior efficacy than *R. trichocarpa* Miguel.

The scientific name of the lacquer tree native to Korea, Japan and China is *Rhus verniciflua* Stokes. Although lacquer has various pharmacological effects, it contains urushiol, which is a known allergen, so it often causes serious allergies such as rashes or itching when ingested directly or upon contact with leaves and sap thereof. Therefore, lacquer should be carefully consumed or used. Recently, techniques for removing the urushiol component have been developed, but a problem of deteriorated efficacy upon removal of the urushiol component has been pointed out.

Meanwhile, lacquer tree is useful as a material for food and pharmaceuticals, but the drawback thereof has been pointed out that the absorption rate of useful ingredients contained in the lacquer tree is very low. Therefore, it is time to develop a method for improving the absorption of useful ingredients of the lacquer tree extract.

In general, a *Rhus verniciflua* Stokes extract is known to contain fustin, fisetin, sulfuretin, butane, and the like as flavonoids. Among these, fustin is generally found in the highest content. However, the result of research showed that fustin has low anticancer activity and fisetin has the highest anticancer activity. Therefore, it is necessary to increase the content of fisetin in order to improve the anticancer activity of the *Rhus verniciflua* Stokes extract. In general, when using an organic synthesis method, fustin can be converted into fisetin. However, it is commonly known that a number of chemicals must be used during this conversion process, and the conversion efficiency is not high. Thus, finding a method for converting fustin into fisetin without using an organic solvent such as acetone or hexane is an important task in obtaining a *Rhus verniciflua* Stokes extract with excellent anticancer activity.

Although a catalyst is involved in the reaction, it is not included as an actual ingredient, and is generally used to lower the reaction energy by controlling the chemical reaction. Accordingly, while contemplating a method of increasing the content of fisetin in *Rhus verniciflua* Stokes, the present inventors conceived a method of converting fustin to fisetin using such a catalyst, and for this purpose, prepared a *Rhus verniciflua* Stokes extract containing a great amount of fisetin by developing a process using a related catalyst, and found that the extract has activity as an anticancer agent that inhibits metastasis of cancer cells. Based on this finding, the present invention has been completed.

DISCLOSURE

Technical Problem

Therefore, the present invention has been made to solve the above problems, and it is one object of the present invention to provide a method of preparing a *Rhus verniciflua* Stokes extract that exhibits an improved anticancer effect through an increased amount of fisetin by developing a method for converting fustin, which is a water-soluble flavonoid contained in the *Rhus verniciflua* Stokes extract, to fisetin having superior anticancer activity.

It is another object of the present invention to provide an anticancer pharmaceutical composition or functional health food that exhibits excellent physiological activity and inhibits metastasis of cancer based on remarkably improved anticancer activity using the *Rhus verniciflua* Stokes extract containing an increased amount of fisetin.

Technical Solution

In accordance with an aspect of the present invention, the above and other objects can be accomplished by the provision of a method for preparing a *Rhus verniciflua* Stokes extract with an increased content of fisetin, the method including adding at least one catalyst selected from the group consisting of platinum, chromium, nickel, silicon, copper, and oxides of these metals, to a *Rhus verniciflua* Stokes extract or a concentrated *Rhus verniciflua* Stokes extract and conducting reaction to convert fustin contained in the *Rhus verniciflua* Stokes into fisetin.

In accordance with another aspect of the present invention, provided is a *Rhus verniciflua* Stokes extract having increased content of fisetin prepared by the method.

In accordance with another aspect of the present invention, provided is a functional health food composition for preventing or ameliorating cancer, or an anticancer pharmaceutical composition for inhibiting metastasis of cancer, as a main component, containing the *Rhus verniciflua* Stokes extract.

Hereinafter, the present invention will be described in detail.

The present invention provides a method for preparing a *Rhus verniciflua* Stokes extract with increased content of fisetin including adding at least one catalyst selected from the group consisting of platinum, chromium, nickel, silicon, copper, and oxides of these metals, to a *Rhus verniciflua*

Stokes extract or a concentrated *Rhus verniciflua* Stokes extract and conducting reaction to convert the fustin contained in the *Rhus verniciflua* Stokes into fisetin.

In addition, in the method for preparing the *Rhus verniciflua* Stokes extract having increased content of fisetin, the catalyst, which is a metal or an oxide of a metal, is preferably added in its native form or in a form impregnated in a support to the *Rhus verniciflua* Stokes extract or the concentrated *Rhus verniciflua* Stokes extract, and the catalyst is preferably added thereto in the step selected from the group consisting of during extraction of the *Rhus verniciflua* Stokes extract, after completion of the extraction and after concentration of the extract.

In addition, in the method for preparing the *Rhus verniciflua* Stokes extract having increased content of fisetin, the method may further include removing oxygen and bubbling an inert gas in order to suppress oxidation of the catalyst during the catalytic reaction of the catalyst with the *Rhus verniciflua* Stokes extract.

The present invention provides a *Rhus verniciflua* Stokes extract having increased content of fisetin prepared by the method.

The present invention provides a functional health food composition for preventing or ameliorating cancer, or an anticancer pharmaceutical composition for inhibiting metastasis of cancer, as a main component, containing the *Rhus verniciflua* Stokes extract.

In the anticancer pharmaceutical composition of the present invention, the cancer, the metastasis of which is inhibited, is preferably a carcinoma selected from the group consisting of gastric cancer, liver cancer, colon cancer, lung cancer, breast cancer, rectal cancer, hematologic cancer and pancreatic cancer.

In general, it is known that the *Rhus verniciflua* Stokes extract contains about 5 to 20% by weight of fustin and about 0 to 5% by weight of fisetin. This is a general method known in the field of organic synthesis, and no method for converting fustin to fisetin that has little effect on other ingredients while maintaining the antioxidant activity of flavonoids is known. In general, oxidation means that a target component is oxidized upon contact with oxygen, and natural extracts have antioxidant activity, but excessively contact oxygen, thus resulting in lowered antioxidant activity. The process of converting fustin to fisetin is not a general oxidation process, but is a reduction process involving the addition of hydrogen.

According to the present invention, the antioxidant activity of the extract is not lowered but rather improved by the method using a catalyst, conditions for converting fustin to fisetin, which cannot be converted through conventional methods, are secured, and an anticancer agent composition having inhibitory activity against metastasis of cancer is found to be developed based thereon.

Advantageous Effects

The present invention provides a very safe and efficient method that is capable of preparing an extract that exhibits improved antioxidant activity and anticancer activity by increasing the content of the main functional ingredients of natural extracts, and an anticancer agent composition prepared by the method. This may be developed into natural-material-based anticancer agents and functional foods which can contribute to improving the health of general population.

BEST MODE

Figure 1:
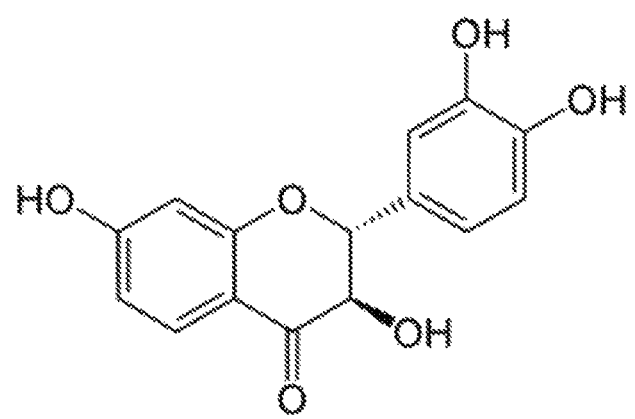
FIG. 1 shows the chemical structural formula of fustin.
Figure 2:
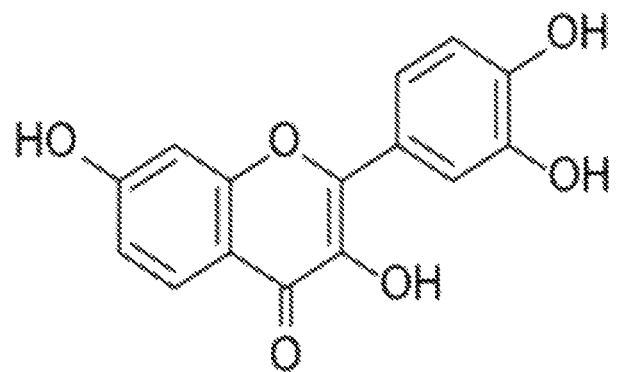
FIG. 2 shows the chemical structural formula of fisetin.

The present invention can be applied while preparing the *Rhus verniciflua* Stokes extract or targeting the prepared extract, or by concentrating and treating the extract, and the catalyst added to facilitate the reaction is removed by filtration during the subsequent filtration process, so the reaction solution can be obtained as an extract with improved physiological activity.

It is considered that there have been no examples of use of catalysts for this purpose on *Rhus verniciflua* Stokes extracts to date. In this respect, the present invention has been conceived based on a novel concept, and relates to a novel process and composition, which cannot be easily developed even by researchers specializing in organic synthesis.

The present invention begins with the preparation of a *Rhus verniciflua* Stokes extract. One or more of platinum, copper, chromium, silicon, and nickel, and most preferably, one or more of platinum and chromium, can be used as the catalyst for the conversion of fustin to fisetin, which is the main target process of the present invention. These metals may be used in the form of pure metals, oxides and nitrogen oxides, and all of them have effects of promoting the reaction, with only a difference in degree therebetween. In general, pure metals exhibit the best effects, followed by oxides and nitrogen oxides. In addition, these catalysts may be produced by coating the surface of the pores of, as a support, a porous material such as activated carbon or zirconia in order to more efficiently conduct the reaction over an increased reaction surface area, and are then added. In this manner, it is possible to apply a conventional method using a catalyst that maximizes the progress of the reaction while minimizing the amount of the catalyst that is used by increasing the reaction surface area by several hundred times. In addition, in some cases, the surface of the vessel for performing the reaction may also be coated with such a metal. The catalyst can be prepared by a conventional method which includes dissolving a metal or oxide thereof in a solvent, immersing a support therein, and then drying the support to support the metal component on the support. The resulting product is added and used as the catalyst.

In general, water extract or diluted ethanol can be used for the preparation of the *Rhus verniciflua* Stokes extract, and the extraction temperature is 50 to 80° C. in the case of containing ethanol, and 60 to 100° C. in the case of water extraction. Temperatures above the range defined above are also possible within the applicable range of a system. The solvent used is generally about 4 to about 10 times the weight of the *Rhus verniciflua* Stokes that is generally fed, which is determined in consideration of economic efficiency, and is not related to ensuring that extraction is possible. The extraction time is generally within the range of 4 to hours in consideration of economic efficiency and maximization of extraction efficiency. Regarding the number of extractions that is conducted, when the amount of the solvent is reduced in the primary extraction, secondary or tertiary extraction may be performed.

The catalyst may be added at the same time as extraction, may be added after the extract is isolated through filtration, or may be added after the extract is concentrated.

When the catalyst is added at the same time as extraction, water-soluble fustin is incorporated into the extract and is simultaneously converted to fisetin by the catalyst, which is formed as a precipitate. When the precipitate is caught by the filter and removed during filtration, a portion thereof may be lost. However, there is an advantage in that extraction and conversion are simultaneously conducted. Fisetin formed by precipitation is caught by the filter during the filtration process. In order to increase the recovery rate of fisetin, the fisetin precipitate caught by the filter may be dissolved in alcohol, as a solvent capable of dissolving the same, and may then also be recovered.

When the extract is separately collected and a catalyst is added thereto, conversion can be performed more easily. Since the volume of the solvent is large, the process of controlling the size of the precipitate of fisetin can also be used by controlling the precipitation of fisetin having low solubility. However, the concentrate is different from the extract in that the fisetin is often precipitated during the concentration process, and thus controlling the size of the fisetin crystals is not easy.

Next, the method of conversion in the concentration step is that, when the *Rhus verniciflua* Stokes is concentrated, a trace amount of fisetin is formed by precipitation, but the water-soluble fustin remains dissolved, so it is easy to convert fustin to fisetin through the catalytic action. In addition, the catalytic reaction for converting fustin to fisetin can maximize the efficiency of the reaction and greatly improve the conversion rate, because the fisetin obtained as a result of reaction has low solubility in an aqueous solution and is continuously formed as a precipitate and is isolated from the solution, so the equilibrium of the reaction shifts in a forward direction to actively convert fustin to fisetin. For this purpose, equilibrium in the conversion of fustin to fisetin can also be controlled to actively convert fustin to fisetin by lowering the concentration of fisetin in the reaction solution in a manner that includes circulating some of the components to the outside and performing cooling to induce the formation of fisetin crystals, and then restoring the original state. In addition, because impurities are removed by filtration in advance, a separate filtration process is not required, as in the case of applying a solvent to the extract. However, since the precipitate of fisetin is naturally formed during the concentration process, an additional dissolution/crystal formation process should be performed in order to control the size of the precipitate.

The amount of the catalyst that is added can be a minimum of 0.1% (w/w) to a maximum of 30% (w/w) based on the amount of solids in the extract or concentrate, and this limit is applied simply in consideration of economic efficiency, and is not necessary for ensuring that the reaction occurs. That is, the catalyst is involved in the reaction, but is not lost in the reaction process, so even a very small amount of the catalyst is capable of catalyzing the reaction. However, there may be a problem in that the probability of a collision with molecules involved in the reaction is lowered, it takes a long period of time for conversion, and the conversion rate is lowered. When the catalyst is added in an excessively high amount, the reaction time can be reduced, but the target solution is a composite as an extract and thus may be involved in other unwanted reactions. Moreover, when the catalyst is added in excess, the rate of conversion to fisetin does not continue to increase, but rather, the produced fisetin may be lost, so the content of fisetin tended to decrease.

Therefore, in the present invention, when fustin is converted to fisetin by adding the catalyst, the content of fustin in the final *Rhus verniciflua* Stokes extract is generally 3% (w/w) or less, the content of fisetin therein is maintained within the range of 5 to 20% (w/w), and the final content was found to be greatly influenced by the concentrations of fustin and fisetin contained in the *Rhus verniciflua* Stokes raw material. When the *Rhus verniciflua* Stokes raw material is aged for more than 10 years, the total flavonoid content was remarkably increased, resulting in increased content of fisetin after conversion to fisetin by adding a catalyst.

In addition, the *Rhus verniciflua* Stokes extract converted to fisetin according to the present invention exhibited an increase in antioxidant activity of about 20 to 35% compared to the *Rhus verniciflua* Stokes extract before conversion, which can be expected to result in further improved physiological activity.

In general, the temperature at which the catalyst is added and reacted is in the range of 60 to 100° C. because the reaction rate generally increases as the temperature increases, and the temperature may be 100° C. or higher for a more rapid reaction. The likelihood of occurrence of undesired reactions increases due to excessively high reactivity. In addition, when the temperature is lower than 60° C., the reactivity of the catalyst is lowered, so the reaction time is prolonged, but the progress of the reaction itself is not a problem.

The reaction period of time is varied depending on the temperature and the amount of the catalyst. In general, the reaction period of time is preferably 2 to 6 hours at a reaction temperature of 90° C. when the catalyst is added in an amount corresponding to a ratio of 1 to 10% (w/w) with respect to the solid content.

In general, the presence of oxygen in the reaction, which is one of the reaction conditions, may be determined to hinder the progress of the reaction. The reason for this is that the conversion of fustin to fisetin is a dehydrogenation reaction, so oxygen accelerates the oxidation reaction of the added catalyst, thus reducing the efficiency of the reaction, and as a result, the yield of fisetin can be reduced. Therefore, oxygen is preferably removed, and the method therefor may include performing purging using an inert gas such as nitrogen or applying a vacuum.

When the catalytic reaction is completed, cooling is conducted. In this process, the finely precipitated fisetin crystals including the dissolved fisetin grow slowly and increase in size. Therefore, to recover the fisetin and to remove the catalyst, the reaction solution is concentrated to adjust the concentration of solid content to more than 50% (w/v), and then pure ethanol is added, and the solution is then heated to completely dissolve the fisetin and then filtered to remove the catalyst. Then, when the filtrate is concentrated to remove the solvent, a *Rhus verniciflua* Stokes extract free of the catalyst and containing an increased amount of fisetin can be obtained.

The *Rhus verniciflua* Stokes extract having increased amount of fisetin thus obtained can be used as an anticancer agent or functional food that inhibits the metastasis of cancer.

In addition, the *Rhus verniciflua* Stokes extract with increased amount of fisetin prepared in the present invention is mixed as a liquid or powder form with excipients, such as saccharides, lecithin, cellulose or the like, generally used in the preparation of food and pharmaceuticals, to prepare compositions of various formulations containing a *Rhus verniciflua* Stokes powder.

Meanwhile, the present invention provides an anticancer agent composition containing a *Rhus verniciflua* Stokes powder extract having increased content of fisetin. The term "comprising" means adding an amount of an extract that enables fisetin to exert anticancer efficacy to the anticancer agent composition of the present invention.

The anticancer composition according to the present invention may contain a pharmaceutically effective amount of *Rhus verniciflua* Stokes extract alone, or may contain the *Rhus verniciflua* Stokes extract in combination with one or more pharmaceutically acceptable vehicles, excipients, or diluents. As used herein, the term "pharmaceutically effective amount" refers to an amount sufficient to prevent, ameliorate and treat cancer symptoms.

The pharmaceutically effective amount of the *Rhus verniciflua* Stokes extract according to the present invention is 0.5 to 100 mg/day/kg of body weight, preferably 0.5 to 5 mg/day/kg of body weight. However, the pharmaceutically effective amount may be appropriately changed according to the degree of cancer symptoms, age, weight, state of health, gender, administration route, and treatment period of the patient.

In addition, as used herein, the term "pharmaceutically acceptable" means physiologically acceptable and that adverse reactions such as gastrointestinal disorders, dizziness, or similar reactions thereto do not occur when administered to a human. Meanwhile, examples of the vehicle, excipient or diluent include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oils. In addition, the anticancer composition according to the present invention may further include a filler, an anticoagulant, a lubricant, a wetting agent, a flavoring agent, an emulsifier, a preservative or the like.

Meanwhile, the composition according to the present invention may be formulated in accordance with a method well-known in the art to provide rapid, sustained or delayed release of the active ingredient after administration to a mammal. Specific examples of the formulation may be a powder, granule, tablet, emulsion, syrup, aerosol, soft or hard gelatin capsule, sterile injectable solution, or sterile powder.

The anticancer composition according to the present invention can be administered through any of various routes including oral, transdermal, subcutaneous, intravenous or intramuscular routes, and the dosage of the active ingredient may be appropriately selected depending on several factors such as the route of administration, and the patient's age, gender, weight, and severity. In addition, the anticancer composition of the present invention can be administered in combination with a known compound having an effect of preventing, ameliorating or treating cancer symptoms. Accordingly, the present invention can provide a drug for preventing and/or treating cancer symptoms containing the *Rhus verniciflua* Stokes extract as an active ingredient.

Furthermore, the anticancer composition according to the present invention not only provides an effect of alleviating cancer symptoms through excellent anticancer and antioxidant activities, but can also be added to foods for the purpose of preventing and ameliorating cancer symptoms, so the composition of the present invention can also be used as a food composition for preventing and ameliorating cancer symptoms. Therefore, the composition of the present invention can be easily utilized as a food effective in preventing and ameliorating cancer symptoms, for example, as a main ingredient or an auxiliary ingredient of a food, a food additive, a functional food or a beverage.

In the present invention, the "food" refers to a natural product or processed product containing one or more nutrients, and preferably means a product in a state that can be eaten directly after a certain degree of processing. Generally speaking, "food" refers to all foods, food additives, functional foods and beverages.

Examples of foods to which the anticancer composition according to the present invention can be added include various foods, beverages, gums, teas, vitamin complexes, functional foods and the like. In addition, examples of foods that can be used in the present invention include, but are not limited to, special nutritional foods (e.g., formulated milk, infant food, and baby food), processed meat products, fish products, tofu, muk (jellied food), noodles (e.g., ramen, noodles, etc.), bread, health supplements, seasoned foods (e.g., soy sauce, miso, red pepper paste, mixed sauce, etc.), sauces, confectioneries (e.g. snacks), candies, chocolates, gums, ice creams, dairy products (e.g. fermented milk, cheese, etc.), other processed foods, Kimchi, pickled foods (e.g. various kinds of Kimchi, pickles, etc.), beverages (e.g., fruit drinks, vegetable drinks, soy milk, fermented drinks, etc.), and natural seasonings (e.g., ramen soup base, etc.). The food, beverage or food additive may be prepared by a conventional production method.

In addition, the term "functional food" refers to a group of foods to which value is added using physical, biochemical and biotechnological techniques to activate and express the function of the food for a specific purpose, or a food, specifically, a health functional food, that is designed and processed to sufficiently express the body regulation functions of the food composition for controlling the biological defense rhythm, and preventing and recovering diseases. The functional food may include a cytologically acceptable food supplement, and may further include suitable vehicles, excipients and diluents commonly used in the production of functional foods.

In addition, the "beverage" is a generic term for a drink for quenching thirst or for providing an enjoyable taste, and includes functional beverages. The beverage has no particular limitation as to other ingredients thereof, as long as the composition for preventing and ameliorating cancer symptoms is contained at the predetermined ratio as an essential ingredient, and may further contain, as additional ingredients, various flavoring agents or natural carbohydrates.

Furthermore, in addition to ingredients described above, the food containing the composition of the present invention may include various nutrients, vitamins, minerals (electrolytes), flavoring agents such as synthetic and natural flavoring agents, coloring agents and fillers (cheese, chocolate, etc.), pectic acid and salts thereof, alginic acid and salts thereof, organic acids, protective colloidal thickeners, pH adjusters, stabilizers, preservatives, glycerin, alcohols, carbonizing agents used in carbonated beverages, and the like, and the components may be used independently or in combination.

In the food containing the anticancer composition of the present invention, the amount of the composition according to the present invention may be 0.001% to 100% by weight, preferably 0.1% to 40% by weight, based on the total food weight. The beverage may contain the composition in an amount of 0.001 g to 5 g, preferably 0.01 g to 2 g, based on 100 mL, but may contain the composition in an amount less than the above range in the case of long-term intake for the purpose of health and hygiene or health control. Since there is no problem in terms of safety, the active ingredient is not limited to the above range and it can be used in an amount greater than the above range.

Therefore, the present invention provides a health functional food for preventing or ameliorating a cancer disease containing the *Rhus verniciflua* Stokes extract according to the present invention as an active ingredient, and the form of the food may be a powder, granule, tablet, capsule or beverage, but is not limited thereto.

Meanwhile, the formulation of the anticancer composition according to the present invention may be prepared in a suitable form depending on the method of use, and may be prepared in accordance with a method well-known in the art to provide rapid, sustained or delayed release of the active ingredient, particularly after administration to a mammal.

Specific examples of the formulation include at least one selected from plasters, granules, lotions, liniments, lemonades, aromatic waters, syrups, ophthalmic ointments, liquids and solutions, aerosols, extracts, elixirs, ointments, fluid extracts, emulsions, suspensions, decoctions, infusions, ophthalmic solutions, tablets, suppositories, injections, spirits, cataplasms, capsules, creams, troches, tinctures, pastes, pills, soft or hard gelatin capsules, coated tablets, powders, granules, and capsules.

In the case of preparing coated tablets, talc, hydroxypropyl methylcellulose and polyethylene glycol are added to the *Rhus verniciflua* Stokes extract having increased content of fisetin as a main component, and are then mixed and tableted by a known method, or lactose, magnesium stearate, colloidal dioxide silicon, hydroxypropyl methylcellulose, polyethylene glycol, and titanium oxide are added thereto, and are then mixed and tableted by a known method.

In the case of preparing a powder, white sugar, lactose, and microcrystalline cellulose are added to the *Rhus verniciflua* Stokes extract having increased content of fisetin as a main component, and the powder is prepared by a known method, or mannitol, corn starch, and colloidal silicon dioxide are added to the main component, and the powder is prepared by a known method.

In the case of preparing a granule, white sugar and corn starch are added to the *Rhus verniciflua* Stokes extract having increased content of fisetin as a main component, and the granule is prepared by a known method, or mannitol, lactose, povidone, and colloidal silicon dioxide are added to the main ingredient and then the granule is prepared by a known method.

In the case of preparing a capsule, microcrystalline cellulose, corn starch, hydroxypropyl cellulose, and magnesium stearate are added to the *Rhus verniciflua* Stokes extract having increased content of fisetin as a main component, and the capsule is prepared by a known method, or lactose, povidone, colloidal silicon dioxide, talc, and magnesium stearate are added to the main component and the capsule is prepared by a known method.

Meanwhile, the dosage of the pharmaceutical composition of the present invention may be determined in consideration of the administration method, the age, gender and weight of the patient, and the severity of the disease. For example, the pharmaceutical composition may be orally administered one or more times at 0.1 to 100 mg/kg (body weight) of the active ingredient per day. However, the dosage is merely an example for illustration, and may be changed by physician depending on the severity and state of the patient.

Hereinafter, the present invention will be described in more detail with reference to the following examples, but the scope of the present invention is not limited to the examples, and includes variations and technical concepts equivalent thereto.

Example 1

10 kg of domestic *Rhus verniciflua* Stokes was purchased from Gyeongdong Market and then sufficiently dried, 90 L of water was added thereto, and the resulting product was extracted at 95° C. for 6 hours, the filtrate was filtered, concentrated in a vacuum and powderized to obtain 580 g of a *Rhus verniciflua* Stokes extract powder (referred to as Sample 1).

100 g of Sample 1 above was dissolved again in 5 equivalents of water and heated to 95° C., 10 g of a chromium powder (100 mesh) as a catalyst was added thereto, and a reaction was conducted for 6 hours, and then 2,000 ml of alcohol was added to dissolve the precipitated fisetin, and the solution was mixed and filtered through a 0.5 μm filter to remove insoluble substances including the catalyst, and the residue was then concentrated and powderized to obtain 93 g of a powder (referred to as Sample 2).

Next, 100 g of Sample 1 was dissolved in 5 equivalents of water and heated to 95° C., 1 g of a chromium catalyst (10% (w/w) of chromium/support as a weight ratio) supported on activated carbon as a catalyst was added thereto, the reaction was conducted for 6 hours, 2,000 ml of alcohol was added thereto to dissolve the precipitated fisetin, and the solution was mixed and filtered through a 0.5 um filter to remove insoluble substances including the catalyst, and then the residue was concentrated and powderized to obtain 94.5 g of a powder (referred to as Sample 3).

Next, 10 g of 6 pieces of Sample 1 were dissolved in 5 equivalents of water and heated to 95° C., and 1 g of each of platinum, chromium oxide ($Cr_2O_3$), $(NH_4)_2CrO_4$, copper, nickel and silicon powders as catalysts was added thereto, the reaction was conducted for 6 hours, 200 ml of alcohol was added thereto to dissolve the precipitated fisetin, and the solution was mixed, filtered through a 0.5 μm filter to remove insoluble substances including the catalyst, and the residue was concentrated and powderized to obtain 9.8 g, 9.3 g, 9.7 g, 9.8 g, 9.9 g, and 9.9 g of powders (referred to as Samples 4, 5, 6, 7, 8, and 9, respectively).

Comparative Example 1

In order to compare the difference with the prior art, as in Example 1 above, 1 kg of *Rhus verniciflua* Stokes was sufficiently dried, 10 L of water was added thereto, extraction was conducted for 6 hours at 95° C., and the extract was filtered and concentrated in vacuum to obtain 610 ml of a concentrated solution when the solid content reached 10.5 Bx. The concentrate was treated at 90° C. for 3 hours while bubbling oxygen a glass flask, and was powderized to finally obtain 57 g of a powder (referred to as Comparative Example 1).

For analysis of the content, fustin and fisetin were analyzed by high-performance liquid chromatography. Here, the analysis conditions were commonly known flavonoid analysis conditions. The results are shown in Table 1 below.

TABLE 1

|  | Fustin (%) | Fisetin (%) | Conversion (%) |
| --- | --- | --- | --- |
| Sample 1 (extract) | 12.1 | 1.7 | — |
| Sample 2 (chromium powder) | 5.6 | 7.5 | 47.9 |
| Sample 3 (chromium support) | 2.2 | 9.4 | 63.6 |
| Sample 4 (platinum) | 1.8 | 10.8 | 75.2 |
| Sample 5 (chromium oxide) | 6.6 | 4.9 | 26.4 |
| Sample 6 ($(NH_4)_2CrO_4$) | 7.8 | 4.0 | 19.0 |
| Sample 7 (copper) | 6.3 | 4.5 | 23.1 |

TABLE 1-continued

|  | Fustin (%) | Fisetin (%) | Conversion (%) |
|---|---|---|---|
| Sample 8 (nickel) | 7.0 | 3.7 | 16.5 |
| Sample 9 (silicon) | 8.2 | 4.2 | 20.7 |
| Comparative example 1 (oxygen treatment) | 11.5 | 1.8 | 0.8 |

The conversion rate was calculated as (fisetin increment/initial fustin content)×100.

As shown in Table 1 above, the method presented in the present invention exhibits a notably high rate of conversion of fustin to fisetin compared with the conventional method.

Example 2

In order to compare the difference in the conversion rate depending on the step of adding the catalyst, an extract was prepared using 10 kg of the *Rhus verniciflua* Stokes extract in the same manner as in Example 1, 1 L of the extract was filtered and concentrated to adjust the solid content thereof to 11.2% (w/v), the chromium catalyst supported on the activated carbon (the same as in Sample 3 of Example 1) was added in an amount of 1% (w/w) with respect to the solid content and then reacted in the same manner as above, and 250 ml of alcohol was added thereto to dissolve the fisetin, and the solution was filtered and then powderized to finally obtain 57.3 g of a *Rhus verniciflua* Stokes extract having increased content of fisetin. As a result of analysis of the extract through high-speed liquid chromatography, the content of fisetin was found to be 9.9% (w/w), and the conversion rate to fisetin was found to be 68%.

Example 3

Figure 3:
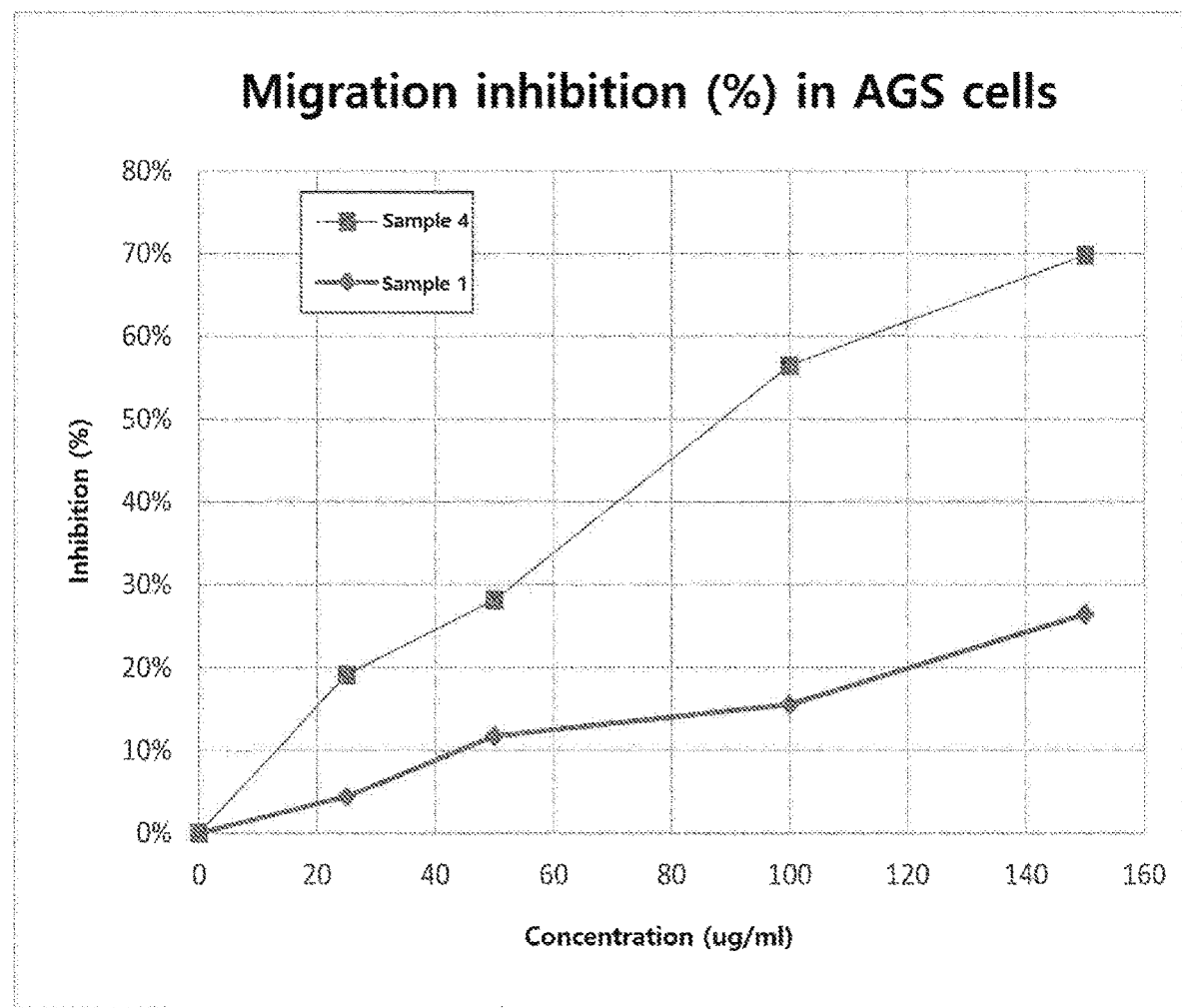
FIG. 3 is a graph comparing the efficacy of inhibiting cancer cell metastasis of *Rhus verniciflua* Stokes extracts prepared in Example of the present invention.

The anticancer activity of the samples obtained above was compared depending on the increased fisetin content. In general, a method of comparing adhesion, invasion and migration is mainly used to determine the efficacy of inhibition of cancer metastasis. In the present invention, the efficacy of inhibition of cancer metastasis was compared between Samples 1 and 4. FIG. 3 shows the results of comparison of metastasis inhibition in gastric-cancer-derived cells, namely AGS cells. Sample 4 of the present invention, which is an extract of *Rhus verniciflua* Stokes extract having increased content of fisetin, exhibits an improved result of remarkably inhibiting metastasis of gastric-cancer-derived AGS cells compared to Sample 1 of the untreated group. Therefore, it was proven that the *Rhus verniciflua* Stokes extract prepared according to the method of the present invention exhibits an effect of inhibiting metastasis of cancer.

INDUSTRIAL APPLICABILITY

The present invention relates to a method for preparing a *Rhus verniciflua* Stokes extract having increased content of fisetin and having more potent anticancer activity and a composition containing the extract, which can be developed as a health functional food, a functional food material, a natural anticancer agent or the like, and as a drug that has the effect of inhibiting cancer metastasis without side effects.

The invention claimed is:

1. A method for preparing a *Rhus verniciflua* Stokes extract, the method comprising adding at least one catalyst selected from the group consisting of platinum, chromium, nickel, silicon, copper, and oxides of these metals to a *Rhus verniciflua* Stokes extract or a concentrated *Rhus verniciflua* Stokes extract and conducting reaction to convert fustin contained in the *Rhus verniciflua* Stokes into fisetin.

2. The method according to claim 1, wherein the catalyst, which is the metal or an oxide of the metal, is added in a native form thereof or in a form impregnated in a support to the *Rhus verniciflua* Stokes extract or the concentrated *Rhus verniciflua* Stokes extract.

3. The method according to claim 1, wherein the catalyst is added to the *Rhus verniciflua* Stokes extract or the concentrated *Rhus verniciflua* Stokes extract at a time selected from the group consisting of during extraction of the *Rhus verniciflua* Stokes extract, after completion of the extraction, and after concentration of the extract.

4. The method according to claim 1, further comprising bubbling an inert gas during a catalytic reaction of the catalyst with the *Rhus verniciflua* Stokes extract or the concentrated *Rhus verniciflua* Stokes extract.

5. A *Rhus verniciflua* Stokes extract prepared by the method according to claim 1.

6. A functional health food composition for preventing or ameliorating cancer comprising, as a main component, the *Rhus verniciflua* Stokes extract according to claim 5.

7. An anticancer pharmaceutical composition for inhibiting metastasis of cancer comprising, as a main component, the *Rhus verniciflua* Stokes extract according to claim 5.

8. The anticancer pharmaceutical composition according to claim 7, wherein the cancer, the metastasis of which is inhibited, is a carcinoma selected from the group consisting of gastric cancer, liver cancer, colon cancer, lung cancer, breast cancer, rectal cancer, hematologic cancer and pancreatic cancer.

9. A method of treating cancer or inhibiting metastasis of cancer, comprising
administering to a subject in need thereof an effective amount of an anticancer pharmaceutical composition for inhibiting metastasis of cancer comprising, as a main component, a *Rhus verniciflua* Stokes extract, the *Rhus verniciflua* Stokes extract prepared by adding at least one catalyst selected from the group consisting of platinum, chromium, nickel, silicon, copper, and oxides of these metals to a *Rhus verniciflua* Stokes extract or a concentrated *Rhus verniciflua* Stokes extract and conducting reaction to convert fustin contained in the *Rhus verniciflua* Stokes into fisetin.

* * * * *